US012668555B2

(12) United States Patent
Zong et al.

(10) Patent No.: US 12,668,555 B2
(45) Date of Patent: Jun. 30, 2026

(54) METHOD FOR PREPARING ETHYLENE PROPYLENE

(71) Applicants: CHINA PETROLEUM & CHEMICAL CORPORATION, Beijing (CN); SHANGHAI RESEARCH INSTITUTE OF PETROCHEMICAL TECHNOLOGY, SINOPEC, Shanghai (CN)

(72) Inventors: Hongyuan Zong, Shanghai (CN); Xiaohong Li, Shanghai (CN); Guozhen Qi, Shanghai (CN); Hongtao Wang, Shanghai (CN); Zhinan Yu, Shanghai (CN); Yijun Zheng, Shanghai (CN); Li Wang, Shanghai (CN)

(73) Assignees: CHINA PETROLEUM & CHEMICAL CORPORATION, Beijing (CN); SHANGHAI RESEARCH INSTITUTE OF PETROCHEMICAL TECHNOLOGY, SINOPEC, Shanghai (CN)

( * ) Notice: Subject to any disclaimer, the term of this patent is extended or adjusted under 35 U.S.C. 154(b) by 329 days.

(21) Appl. No.: 18/245,381

(22) PCT Filed: Sep. 15, 2021

(86) PCT No.: PCT/CN2021/118395
§ 371 (c)(1),
(2) Date: Mar. 15, 2023

(87) PCT Pub. No.: WO2022/057807
PCT Pub. Date: Mar. 24, 2022

(65) Prior Publication Data
US 2023/0348340 A1 Nov. 2, 2023

(30) Foreign Application Priority Data

Sep. 15, 2020 (CN) .......................... 202010968050.4

(51) Int. Cl.
*C07C 1/22* (2006.01)
*B01J 8/00* (2006.01)
(Continued)

(52) U.S. Cl.
CPC ................. *C07C 1/22* (2013.01); *B01J 8/001* (2013.01); *B01J 8/0015* (2013.01); *B01J 8/007* (2013.01);
(Continued)

(58) Field of Classification Search
CPC ........... C07C 1/22; C07C 11/04; C07C 11/06; C07C 2529/85; C07C 1/20; B01J 8/001;
(Continued)

(56) References Cited

U.S. PATENT DOCUMENTS 3,948,757 A 4/1976 Strother
5,736,107 A 4/1998 Inomata et al.
(Continued)

FOREIGN PATENT DOCUMENTS

CN 101279874 A * 10/2008
CN 101279875 A 10/2008
(Continued)

OTHER PUBLICATIONS

Wang, Hongtao et al.; "Coupling of C4 Alkene Catalytic Cracking and Methanol to Olefins over SAPO-34 Molecular Sieve Catalyst"; Chemical Reaction Engineering and Technoloyg; vol. 29, No. 2, Apr. 30, 2013; pp. 140-146.

*Primary Examiner* — Michelle Stein
(74) *Attorney, Agent, or Firm* — NKL Law; Allen Xue

(57) ABSTRACT
A device for mixing at least two granular materials has a first lifting tube used for loading first particles and a second
(Continued)

lifting tube surrounding and coaxial to the first lifting tube and used for loading second particles. The upper part of said first lifting tube extends beyond the top of said second lifting tube, and at least part of the upper part of the first lifting tube and at least part of the upper part of the second lift tube are located inside a fast bed precipitator, allowing the first and second particles to be transported by means of the first and second lifting tubes to the interior of said fast bed precipitator and mixed.

13 Claims, 6 Drawing Sheets

(51) Int. Cl.

| | |
|---|---|
| *B01J 8/08* | (2006.01) |
| *B01J 8/18* | (2006.01) |
| *B01J 8/26* | (2006.01) |
| *B01J 29/85* | (2006.01) |
| *B01J 29/90* | (2006.01) |
| *B01J 38/02* | (2006.01) |
| *C07C 11/04* | (2006.01) |
| *C07C 11/06* | (2006.01) |

(52) U.S. Cl.
CPC .............. *B01J 8/008* (2013.01); *B01J 8/085* (2013.01); *B01J 8/087* (2013.01); *B01J 8/1827* (2013.01); *B01J 8/1863* (2013.01); *B01J 8/26* (2013.01); *B01J 29/85* (2013.01); *B01J 29/90* (2013.01); *B01J 38/02* (2013.01); *C07C 11/04* (2013.01); *C07C 11/06* (2013.01); *B01J 2208/00017* (2013.01); *B01J 2208/00539* (2013.01); *C07C 2529/85* (2013.01)

(58) Field of Classification Search
CPC . B01J 8/0015; B01J 8/007; B01J 8/008; B01J 8/085; B01J 8/087; B01J 8/1827; B01J 8/1863; B01J 8/26; B01J 29/85; B01J 29/90; B01J 38/02; B01J 2208/00017; B01J 2208/00539; B01J 2208/00176; B01J 8/1809; B01J 8/44; B01J 8/0055; B01J 8/388; C10G 2400/20; C10G 11/18; C10G 11/00; Y02P 20/52; Y02P 20/584; Y02P 30/20; Y02P 30/40
See application file for complete search history.

(56) References Cited

U.S. PATENT DOCUMENTS

| | | | | |
|---|---|---|---|---|
| 6,166,282 | A | * | 12/2000 | Miller .................... C10G 11/18 |
| | | | | 585/641 |
| 2003/0127358 | A1 | | 7/2003 | Letzsch |
| 2004/0076554 | A1 | | 4/2004 | Kuechler et al. |
| 2005/0229491 | A1 | | 10/2005 | Loffler |
| 2006/0025646 | A1* | | 2/2006 | Fung ........................ C10G 3/48 |
| | | | | 585/639 |
| 2006/0059870 | A1* | | 3/2006 | Beech, Jr. ................ C10G 3/57 |
| | | | | 55/345 |
| 2008/0039667 | A1 | | 2/2008 | Vora et al. |
| 2010/0286459 | A1* | | 11/2010 | Gauthier ................ C10G 11/18 |
| | | | | 585/303 |
| 2010/0331596 | A1* | | 12/2010 | Xie ........................... C07C 1/20 |
| | | | | 585/638 |
| 2011/0218373 | A1* | | 9/2011 | Qi .............................. C07C 4/08 |
| | | | | 585/301 |
| 2011/0306811 | A1* | | 12/2011 | Qi ........................... B01J 29/90 |
| | | | | 585/324 |
| 2012/0271088 | A1* | | 10/2012 | Wei ........................ B01J 37/084 |
| | | | | 585/639 |
| 2013/0150233 | A1 | | 6/2013 | Wolschlag et al. |
| 2014/0275675 | A1* | | 9/2014 | Eng ........................ C10G 11/18 |
| | | | | 585/303 |
| 2015/0190773 | A1* | | 7/2015 | Chewter .................. B01J 29/40 |
| | | | | 585/312 |
| 2016/0304413 | A1* | | 10/2016 | Liu ........................... B01J 29/90 |

FOREIGN PATENT DOCUMENTS

| | | | |
|---|---|---|---|
| CN | 101279877 | A | 10/2008 |
| CN | 101348404 | A | 1/2009 |
| CN | 102276398 | A | 12/2011 |
| CN | 102276406 | A | 12/2011 |
| CN | 102372538 | A | 3/2012 |
| CN | 102814151 | A | 12/2012 |
| CN | 103772092 | A | 5/2014 |
| CN | 102464534 | B | 11/2014 |
| CN | 104628506 | A | 5/2015 |
| CN | 107540497 | A | 1/2018 |
| CN | 107540503 | A | 1/2018 |
| CN | 109694294 | A | 4/2019 |
| CN | 110117214 | A | 8/2019 |
| CN | 111056902 | A | 4/2020 |
| EP | 1140743 | B1 | 10/2005 |
| EP | 2334760 | B1 | 10/2014 |
| WO | 2014005997 | A1 | 1/2014 |
| WO | 2016109367 | A1 | 7/2016 |

* cited by examiner

METHOD FOR PREPARING ETHYLENE PROPYLENE

TECHNICAL FIELD

The present invention relates to a process for producing ethylene-propylene.

BACKGROUND

Lower olefins, namely ethylene and propylene, are two important basic chemical raw materials, and the demand of the lower olefins is increasing continuously. In recent years, the process of Methanol to Olefins (MTO) has been greatly developed, and three technologies have been industrially applied, and many related patents exist.

CN102464534B and CN102372538A disclose zoned processes of MTOs, wherein methanol enters a lower premixing zone or a catalyst mixing tube and an upper main reaction zone respectively for reaction.

In the process disclosed in CN102276398A, liquid methanol enters an initial contacting zone to exchange heat with a spent catalyst, and then goes upward to enter a main reaction zone to react to generate ethylene and propylene.

According to the scheme above, as the reaction conditions in the premixing area, the catalyst mixing tube and the initial contacting area are not suitable for methanol conversion, the carbon-based loss of methanol is caused, and the selectivity to the both olefins is low. In particular, in MTO processes, particulate catalysts are involved in deactivation (especially, for example, coking) and regeneration, while a certain extent of coking of the catalyst may be beneficial to the reaction. Thus, in an MTO process, it is desirable to rapidly mix a regenerated catalyst with a coked-deactivated catalyst in a certain ratio.

SUMMARY OF THE INVENTION

One of the technical problems to be solved by the present invention is to overcome the technical defect of low ethylene-propylene selectivity in the prior art, and to provide a reaction process for producing ethylene-propylene, which has the advantage of high ethylene-propylene selectivity.

In order to solve the problem above, the present invention provides a general process for producing ethylene-propylene, comprising:

a) feeding a methanol feedstock into the bottom of a fast bed reactor to be contacted and reacted with a catalyst to obtain a reaction product I and a first particulate catalyst obtained from partial inactivation of the catalyst, both being delivered upward into a fast bed settler;

b) feeding an oxygenate feedstock and/or a light hydrocarbon feedstock into the bottom of an outside riser reactor to be contacted and reacted with a regenerated catalyst to obtain a reaction product II and a second particulate catalyst, both being delivered upward into a riser settler;

c) feeding a second part of the second particulate catalyst into the bottom of the riser, which is optionally contacted and reacted with the oxygenate feedstock and/or the light hydrocarbon feedstock, to produce a mixture of a reaction product III and a third particulate catalyst, wherein the second particulate catalyst or optionally the mixture of the reaction product III and the third particulate catalyst are delivered upward into the fast bed settler;

d) mixing the first particulate catalyst with the second particulate catalyst or optionally with the third particulate catalyst in the fast bed settler to obtain a mixed catalyst, and feeding a first part of the mixed catalyst and a first part of the second particulate catalyst into a regenerator respectively for regeneration to obtain the regenerated catalyst; and wherein the oxygenate feedstock contains water and oxygenates, wherein the oxygenates are present in an amount of from 5 to 60 wt %, and the light hydrocarbon feedstock comprises a C4-C6 non-aromatic hydrocarbon mixture;

wherein the fast bed reactor, the fast bed settler and the riser are coaxially arranged, and the riser is located, in the radial direction, within the fast bed reactor.

Accordingly, the present invention also provides an exemplary specific process for producing ethylene-propylene, comprising:

a-1) feeding a methanol feedstock into a fast bed reactor to be contacted and reacted with a catalyst to obtain a reaction product I, and delivering upward a first particulate catalyst obtained from partial inactivation of the catalyst into a fast bed settler through a fast bed fast separator;

a-2) for the mixed catalyst in the fast bed settler, feeding a first part thereof into a stripper, returning a second part thereof to the fast bed reactor, and feeding a third part thereof into an outside heat-exchanger to be contacted with a heat-removing medium for cooling followed by being returned to the fast bed reactor;

b-1) feeding a light hydrocarbon feedstock and an oxygenate feedstock into the outside riser reactor to be contacted with the catalyst, for reaction during the upward delivering thereof, and being fed into the riser settler, to obtain a reaction product II and a second particulate catalyst, wherein the oxygenate feedstock contains water and an oxygenate;

c-1) for the second particulate catalyst from the riser settler, feeding a first part thereof into a stripper, and feeding a second part thereof into the riser I; wherein the second particulate catalyst fed into the riser I enters the fast bed settler through the riser fast separator by the lifting of a riser lifting medium;

d-1) feeding the catalyst from the stripper, after being stripped by a stripping medium, into a regenerator to be contacted with a regeneration medium to burn coke on the catalyst to obtain a regenerated catalyst and flue gas;

d-2) degassing the regenerated catalyst and then deeding the degassed regenerated catalyst into the outer riser reactor; and deeding the reaction product I and the reaction product II together into a separation unit to obtain a product rich in ethylene and propylene, $C_4$-$C_6$ non-aromatic hydrocarbon mixture and an aqueous phase, wherein a part or all od the aqueous phase is used as the oxygenate feedstock.

It will be readily understood by those skilled in the art that step a-1) of the exemplary specific process corresponds substantially to step a) of the general process of the invention; similar correspondences exist between steps b) and b-1), c) and c-1), and d) and d-1)/d-2). Therefore, it is understood by those skilled in the art that various technical features referred to in the present application may be applied interchangeably in the substantially corresponding steps of the general process and of the exemplary specific process, unless the purpose of the present invention or the specific purpose of a corresponding embodiment is not satisfied.

Furthermore, the step a-2) of the exemplary specific process is an optionally additional step compared to the general process.

In the present invention, the reaction products referred to in the various embodiments, including, for example, the reaction product I, reaction product II, reaction product III, and additional reaction product, etc., as indicated, each represent a material obtained by a reaction intended to provide products of ethylene and propylene, and capable of providing products rich in ethylene and propylene by means of separation units known in the art, but the specific composition thereof may differ somewhat in the various embodiments due to variations in the starting materials, reaction conditions, etc., within the scope of the present invention.

In the technical solution for producing ethylene-propylene by catalytic conversion of methanol, $C_4$-$C_6$ non-aromatic hydrocarbon and an aqueous solution of oxygenate are contacted and reacted with a regenerated catalyst in the outer riser reactor, and are converted into ethylene and propylene at high selectivity under the conditions of high temperature and high linear velocity, so that the generation of heavy hydrocarbon and phenol compounds is avoided. Meanwhile, the regenerated catalyst obtained is fully mixed with the first particulate catalyst obtained by partial deactivation in the fast bed settler through a special fast separator structure and then is fed into the reaction zone of the fast bed reactor to participate in MTO reaction, so that high selectivity to ethylene and propylene can be obtained.

According to an embodiment of the invention, using the SAPO-34 catalyst, the total yield, based on carbon, of the ethylene and propylene can reach 90.4 wt %, representing a desirable technical effect.

DESCRIPTION OF SOME REFERENCE SIGNS

Figure 1:
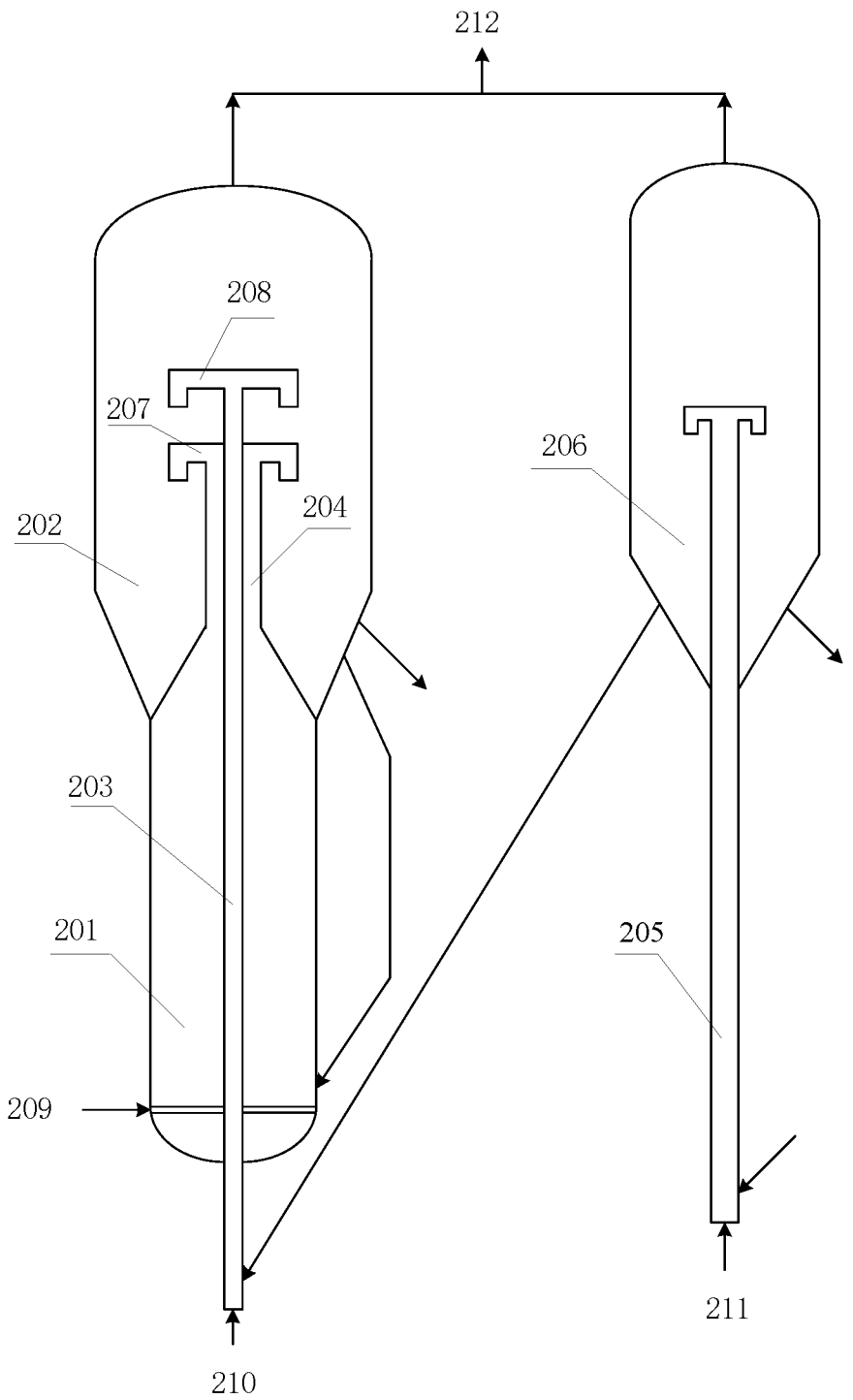
FIG. 1 shows a schematic figure of a reaction system of the process for producing ethylene-propylene according to one embodiment of the present invention.

201 denotes a fast bed reactor; 202 denotes a fast bed settler; 203 denotes a riser; 204 denotes a lifting zone of the fast bed reactor; 205 denotes an outer riser reactor; 206 denotes a riser settler; 207 denotes a fast separator of the fast bed; 208 denotes a riser fast separator; 209 denotes a feed inlet for methanol; 210 denotes an inlet for a riser lift medium; 211 denotes an inlet for a refreshed feedstock; 212 denotes a product outlet;

32 denotes the top of the lower branch pipe of the fast bed separator of the fast bed; 33 denotes a diffuser plate; 34 denotes a diffuser cone;

38 denotes a lower branch pipe of the fast bed fast separator (fast bed fast separator lower branch pipe); 39 denotes a lower branch pipe of the riser fast separator (riser fast separator lower branch pipe); 40 denotes a horizontal pipe of the fast separator; 41 denotes a horizontal pipe of the fast separator of the riser.

EMBODIMENTS

The present invention will be illustrated in detail in the embodiments referring to the drawings. It should be understood that the detailed description and specific Examples, while indicating the preferred embodiments of the invention, are given by way of illustration and explanation only, without limiting the present invention.

In the description of the present invention, it is to be understood that the orientation or position relationship indicated by terms "transverse" direction, "radial" direction, "circumferential" direction, "inner", "outer" and the like refer to the orientation or position relationship in the drawings, which are provided for convenience of easy and simple description, but not to indicate or imply that a device or part so referred to must have a particular orientation, be constructed and operated in a particular orientation, and thus, are not to be considered as limitation to the present invention.

In the present invention, a same reference sign generally denotes the same/corresponding object.

In the present invention, the pressure is gauge pressure unless otherwise specified.

As shown in FIG. 1, the present invention provides a process for producing ethylene-propylene, wherein the reaction system and general flow scheme thereof are shown in the figure. The reaction system thus comprises:

A reaction function zone, comprising: a fast bed reactor 201 having a lifting zone 204 with decreased radius in its upper portion, a fast bed settler 202, a riser 203, optionally an outside heat-exchanger (located outside the mixing device and not shown in the figure); and An outer lifting/regeneration zone comprising: an outer riser reactor 205, a riser settler 206, optionally a stripper (not shown), optionally a regenerator (not shown).

Referring to FIG. 1, in one embodiment, the present invention provides a general process for producing ethylene-propylene, comprising:

a) feeding a methanol feedstock 14 into the bottom of a fast bed reactor 201 to be contacted and reacted with a catalyst to obtain a reaction product I and a first particulate catalyst obtained from partial inactivation of the catalyst, both being delivered upward into a fast bed settler 202;

b) feeding an oxygenate feedstock 15 and/or a light hydrocarbon feedstock 16 into the bottom of an outside riser reactor 205 to be contacted and reacted with a regenerated catalyst to obtain a reaction product II and a second particulate catalyst 10, both being delivered upward into a riser settler 206;

c) feeding a second part 10-2 of the second particulate catalyst into the bottom of the riser 203, which is optionally contacted and reacted with the oxygenate feedstock 15 and/or a light hydrocarbon feedstock 16, to produce a mixture of a reaction product III and a third particulate catalyst, wherein the second particulate catalyst or optionally the mixture of the reaction product III and the third particulate catalyst are delivered upward into the fast bed settler 202;

d) mixing the first particulate catalyst with the second particulate catalyst or optionally with the third particulate catalyst in the fast bed settler to obtain a mixed catalyst 9, and feeding a first part of the mixed catalyst and a first part of the second particulate catalyst into a regenerator respectively for regeneration to obtain the regenerated catalyst.

In one embodiment, both the oxygenate feedstock 15 and the light hydrocarbon feedstock 16 are fed into the outside riser reactor 205, and neither the oxygenate feedstock 15 nor the light hydrocarbon feedstock 16 is fed into the riser 203. Accordingly, in step c), a mixture of reaction product III and the third particulate catalyst is not obtained; while a second part of the second particulate catalyst are directly delivered upward into the fast bed settler 202. This embodiment corresponds to the exemplary specific process of the present invention.

In one embodiment, the light hydrocarbon feedstock 16 is fed into the outside riser reactor 205 and the oxygenate feedstock 15 is fed into the riser 203. Accordingly, in step c), a mixture of the reaction product III and the third particulate catalyst is obtained; which mixture is delivered upward into the fast bed settler 202.

In one embodiment, both the oxygenate feedstock 15 and the light hydrocarbon feedstock 16 are fed into the outside riser reactor 205, and both the oxygenate feedstock 15 and the light hydrocarbon feedstock 16 are fed into the riser 203. Accordingly, in step c), a mixture of the reaction product III and the third particulate catalyst is obtained; which mixture is delivered upward into the fast bed settler 202.

In one embodiment, the oxygenate feedstock 15 is fed into the outside riser reactor 205, and the light hydrocarbon feedstock 16 is fed into the riser 203. Accordingly, in step c), a mixture of the reaction product III and the third particulate catalyst is obtained; which mixture is delivered upward into the fast bed settler 202.

In one embodiment, the riser 203 and the fast bed reactor 201 are coaxial with the fast bed settler 202, the fast bed reactor 201 surrounding the riser 203; the outlet of the riser 203 is connected with a riser outlet structural member 208 (such as a fast separator), and the top of the fast bed reactor 201 is connected with a fast bed outlet structural member 207 (such as a fast separator); the riser fast separator 208 and the fast bed fast separator 207 are both located within the fast bed settler 202. In one embodiment, the riser fast separator 208 is located above the fast bed fast separator 207. In one embodiment, the riser outlet structural member 208 (see FIGS. 6 and 7) is located inside the fast bed fast separator 207, the outer riser reactor 205 is coaxial with the riser settler 206, and the upper portion and the outlet of the outer riser reactor 205 are located inside the riser settler 206.

In one embodiment, the mixed catalyst outlet of the riser settler 206 is communicated with the feed inlet of the riser 203 and is communicated with the feed inlet of the stripper, the mixed catalyst outlet of the fast bed settler 202 is communicated with the feed inlet of the stripper and is communicated with the feed inlet of the outside heat-exchanger, the solid outlet of the stripper is communicated with the solid feed inlet of the regenerator, and the outlet of the heat-removed product of the outside heat-exchanger is communicated with the upper opening of the fast bed settler 202.

In one embodiment, the interior of the fast bed settler 202 is provided with an annular distributor surrounding and coaxial with the upper portion of the outer casing vessel 201 for delivering a fluidizing gas (e.g., steam) upward into the interior of the fast bed settler 202 to act on the first and second particulate catalysts.

In the system of the invention, the aqueous solution of the oxygenate is contacted and reacted with the regenerated catalyst in the outside riser reactor 205, and is converted into lower hydrocarbons under the conditions of high temperature and high linear speed, thereby avoiding the generation of heavy hydrocarbons and phenol compounds. Meanwhile, the regenerated second catalyst obtained is delivered upward and fully mixed with the first particulate catalyst obtained by partial deactivation, and then is fed into the reaction zone of the fast bed reactor to be contacted and reacted with methanol, so that high selectivity to ethylene and propylene can be obtained.

In the present invention, cyclones, or any other device capable of performing a similar function (in particular, such as the separation of catalyst from product) may be provided in both the fast bed settler 202 and riser settler 206.

Figure 2:
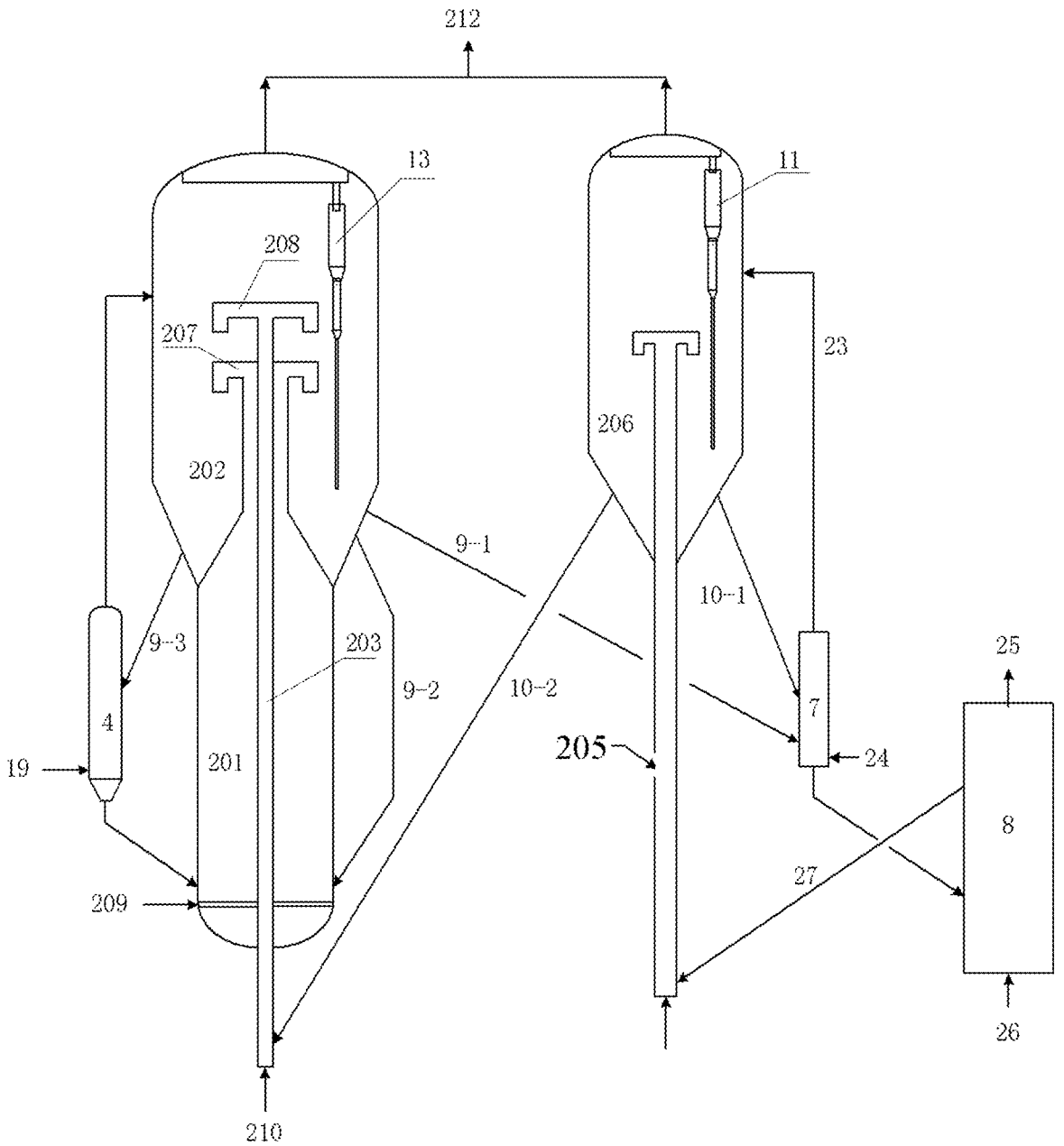
FIG. 2 shows a schematic figure of a reaction system of the process for producing ethylene-propylene according to one embodiment of the present invention.
Figure 3:
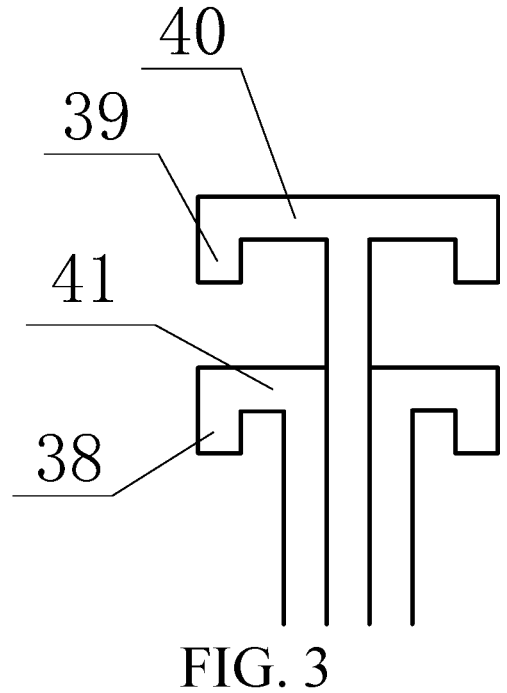
FIGS. 3-5 show schematic figures for the detailed connection of the riser outlet structural member (fast separator) 108 with the outer casing vessel outlet structural member (fast separator) according to an embodiment of the present invention.

Referring to the illustrated embodiments shown in FIG. 1-3, according to one embodiment of the present invention, the riser fast separators 208 is of a branch pipe structure, preferably lower branch pipes 39, and preferably the lower branch pipes 39 are uniformly distributed.

According to one embodiment of the present invention, the fast bed fast separator 207 is of a branch pipe structure, preferably lower branch pipes 38, and preferably the lower branch pipes 38 are uniformly distributed.

According to one embodiment of the invention, the lower branch pipe 39 of the riser fast separator and the lower branch pipe 38 of the fast bed fast separator are distributed crosswise.

According to an embodiment of the present invention, the number, n, of the riser fast separator lower branch pipes 39 of the riser fast separator 208 is 2 to 8; and the included angle, $\beta$, between adjacent riser fast separator lower branch pipes 39 equals to 45-180 degrees. This embodiment is shown, for example, in FIG. 4.

According to an embodiment of the present invention, the number, m, of the fast bed fast separator lower branch pipes 38 of the fast bed fast separator 207 is 2 to 8; and the included angle, $\alpha$, between adjacent fast bed fast separator lower branch pipes 38 equals to 45-180 degrees. This embodiment is shown, for example, in FIGS. 4 and 5.

According to an embodiment of the present invention, the distance from the center point of the fast bed separator 207 to the center point of the fast bed separator lower branch pipe 38 is less than or equal to the distance from the center point of the riser fast separator 208 to the riser fast separator lower branch pipe 39. More preferably, the ratio of the distance from the center point of the fast bed separator 207 to the center point of the fast bed separator lower branch pipe 38 to the distance from the center point of the riser fast separator 208 to the riser fast separator lower branch pipe 39 is 0.3-1:1.

Figure 4:
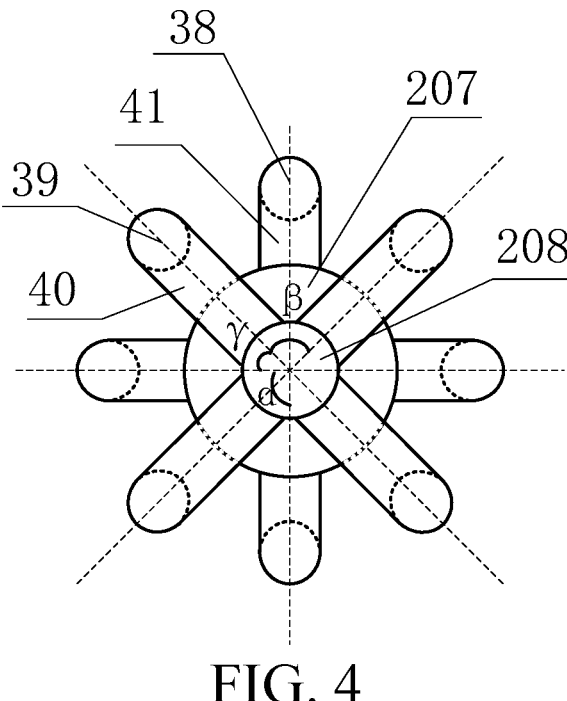
Figure 5:
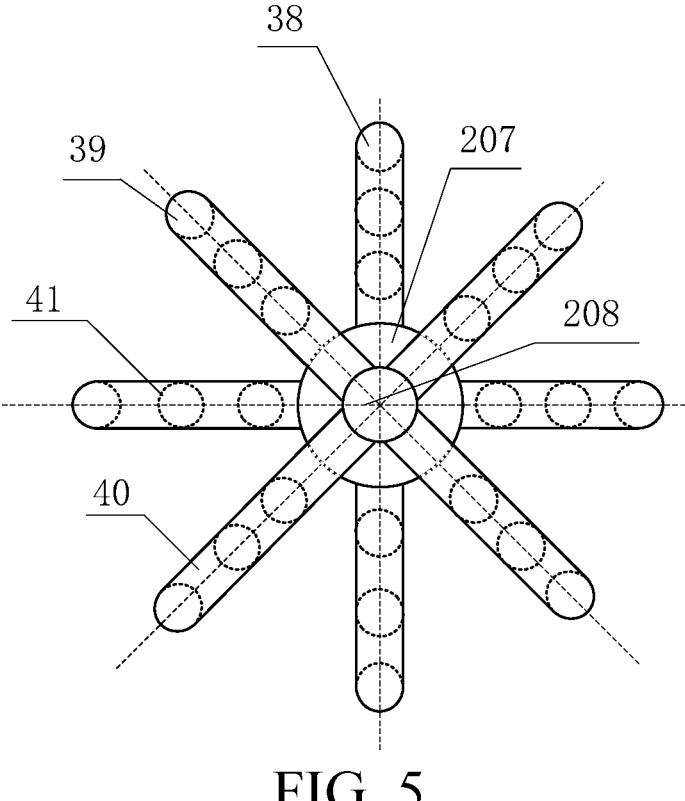

According to an embodiment of the invention, the upper part of the riser 203 extends beyond the top of the lifting zone 204 of the fast bed reactor, so that the riser outlet structural member 208 is located above the fast bed outlet structural member 207. Such embodiments may be referred to as "above-below arrangement" in the present invention, which are illustrated, for example, in FIGS. 1-3. FIGS. 4 and 5 are specific illustrations of the outlet structural member 208 and the fast bed outlet structural member 207 that may be used in this above-below arrangement.

According to an embodiment of the present invention, the riser outlet structural member 208 is located inside the fast bed outlet structural member 207, such that the first particulate catalyst is premixed with the second particulate catalyst inside the fast bed outlet structural member 207. Embodiments that may be referred to as "inside arrangement" in the present invention are illustrated, for example, in FIGS. 6-8.

Similar to the previous discussion about the correspondence of the present invention, in the present invention, the mutual positional arrangement between the riser outlet structural member and the outer casing vessel outlet structural member (fast bed outlet structural member) is not limited to the discussion in each embodiment or the illustration in the corresponding figure(s), while the positional arrangement of the "up-down arrangement" or the "inside arrangement" may be independently selected as described above, unless the purpose of the present invention or the specific purpose of a corresponding embodiment is not satisfied.

Figure 6:
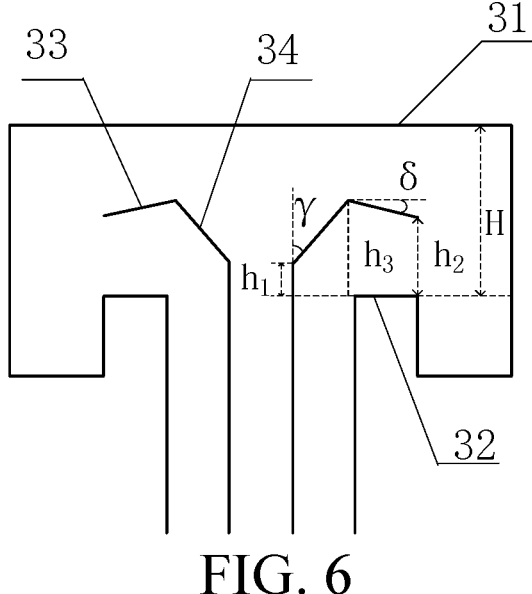
FIGS. 6 and 7 show schematic figures for the specific connection of the riser outlet structural members.

Referring to FIG. 6, according to an embodiment of the present invention, the riser outlet structural member 208 is a flow guiding structure, which is composed of an assembly of a diffusion cone 34 and a diffusion plate 33, the outlet of the riser 203 is connected to the diffusion cone 34, and the diffusion cone 34 is connected to the diffusion plate 33; the distance between the outlet of the riser 203 and the top 32 of the lower branch pipe of the fast bed fast separator is h1, the distance from the connection point of the diffusion cone 34 and the diffusion plate 33 to the top 32 of the lower branch of the fast bed fast separator is h3, the distance between the edge point of the diffusion plate 33 and the top 32 of the lower branch of the fast bed fast separator is h2, and the distance between the top 31 of the fast bed fast separator and the top 32 of the lower branch of the fast separator is H; the included angle between the diffusion cone 34 and the vertical direction is gamma, and the included angle between the diffusion plate 33 and the horizontal direction is δ; the ratio of h1 to H is (0.05-0.3):1, the ratio of h2 to H is (0.2-0.5):1, and the ratio of h3 to H is (0.4-0.6):1; h3 is greater than h2; γ is 10-60 degrees, and δ is 30-80 degrees.

Figure 7:
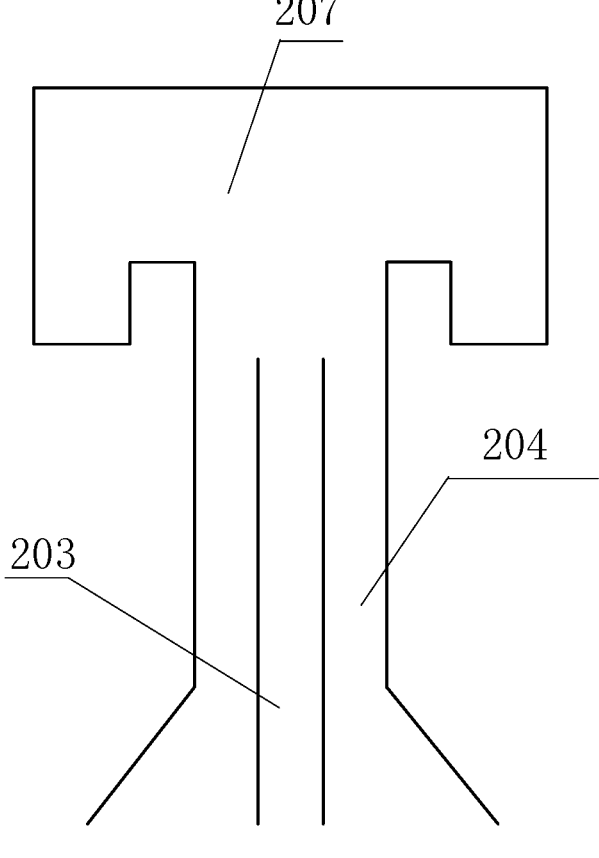

Referring to FIG. 7, according to an embodiment of the invention, the riser outlet structural member 208 adopts the upper portion of the riser 203 directly as a flow guide member.

Figure 8:
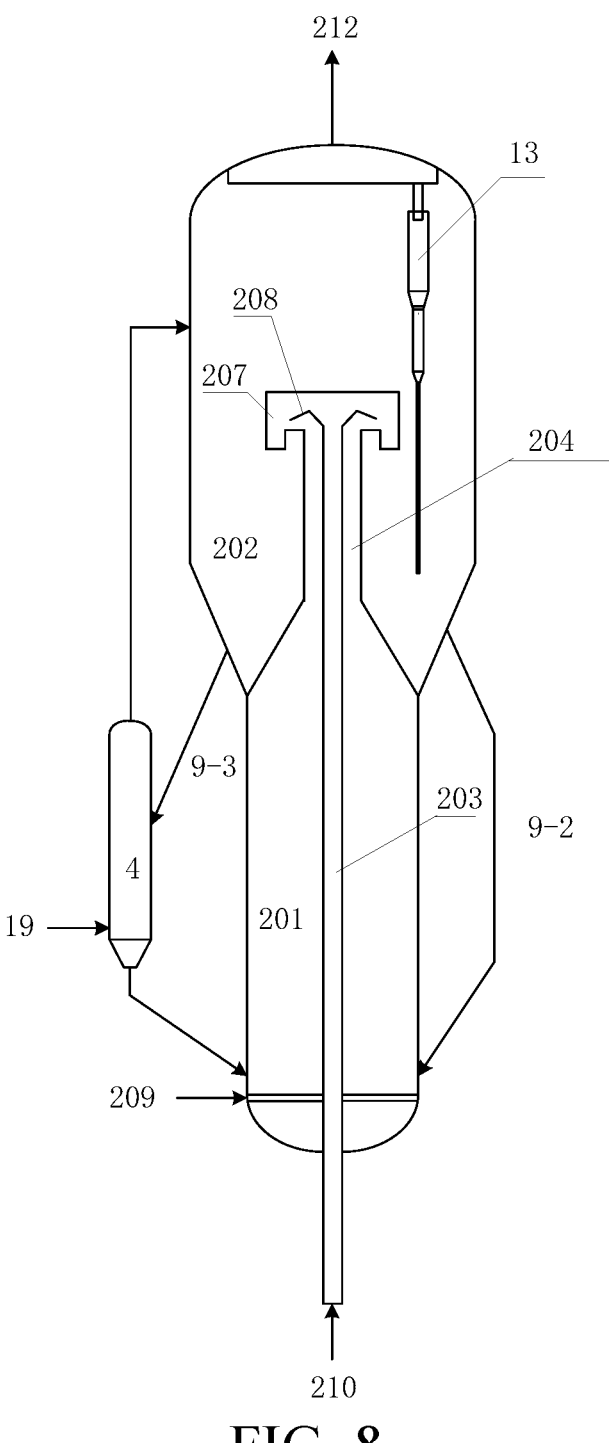
FIG. 8 shows a schematic figure of a mixing device according to one embodiment of the present invention.

Accordingly, referring to FIG. 8, which represents a variation of the mixing device of the present invention as depicted in FIG. 1, which utilizes, for example, the riser outlet structural member 208 and the fast bed outlet structural member 207 in an "inside arrangement" as showed in FIG. 6, and is particularly useful in the system for producing ethylene-propylene as showed in FIG. 2, and particularly as the reaction functional zone of the system. According to this embodiment, the mixing device illustratively comprises an outside heat-exchanger 4 and a cyclone 13.

By using the system of the present invention, the yield of propylene-ethylene is high.

Referring to FIG. 2, it is a preferred embodiment of the reaction system of the present invention as shown in FIG. 1, comprising an outside heat-exchanger 4, a stripper 7 and a regenerator 8. Referring to FIG. 2, according to an embodiment of the present invention, the present invention provides an exemplary specific process for producing ethylene-propylene, the process being carried out in a reaction system according to the present invention, the process comprising:

a-1) feeding a methanol feedstock into the reaction section of a fast bed reactor 201 through a methanol feed inlet 209 to be contacted and reacted with a catalyst to obtain a reaction product I (stream 22), from which a first particulate catalyst obtained from partial deactivation is delivered upward through the upper lifting zone 204 and is fed into a fast bed settler 202 through a fast bed fast separator 207;

a-2) feeding a first part of the mixed catalyst (stream 9-1) from the fast bed settler 202 into a stripper, and returning a second part (stream 9-2) of the mixed catalyst to the reaction section of the fast bed reactor 201, and feeding a third part (stream 9-3) of the mixed catalyst into an outside heat-exchanger 4 to be contacted with a heat-removing medium 19 for cooling followed be being returned to the reaction section of the fast bed reactor 201;

b-1) feeding a light hydrocarbon feedstock and an oxygenate feedstock into the outside riser reactor 205 through the refreshed feedstock inlet 211 to be contacted with the catalyst, for reaction during the upward delivering thereof, and being fed into the riser settler 206, to obtain a reaction product II (stream 21) and a second particulate catalyst (stream 10), wherein the oxygenate feedstock contains water and an oxygenate;

c-1) for the second particulate catalyst from the riser settler 206, feeding a first part (stream 10-1) thereof into a stripper, and feeding a second part (stream 10-2) thereof into the riser 203; wherein the second particulate catalyst fed into the riser 203 enters the fast bed settler 202 through the riser fast separator 208 by the lifting of a riser lifting medium;

d-1) feeding the catalyst from the stripper, after being stripped by a stripping medium 24, into a regenerator to be contacted with a regeneration medium 26 to burn coke on the catalyst to obtain a regenerated catalyst and flue gas 25; and d-2) optionally, degassing the regenerated catalyst and then feeding the degassed regenerated catalyst (stream 27) into the outside riser reactor 205; and feeding the reaction product I and the reaction product II together via the product outlet 212 into a separation unit to obtain a product rich in ethylene and propylene, $C_4$-$C_6$ non-aromatic hydrocarbon mixture and an aqueous phase, wherein a part or all of the aqueous phase is used as the oxygenate feedstock.

According to an embodiment of the invention, the stripper is an independent device. According to an embodiment of the invention, the first part of the mixed catalyst and the first part of the second particulate catalyst are fed into the same stripper.

It will be understood by those skilled in the art that in the present invention, the stripper primarily functions to remove catalyst-entrained impurities, such as entrained reaction oil and gas. Thus, according to an embodiment of the invention, the stripper can be replaced by any other device capable of performing the primary function, as long as it does not significantly damage the purpose of the invention.

It will be understood by those skilled in the art that in the present invention, the primary function of the outside heat-exchanger is to cool the mixed catalyst, to fit the needs of the reaction in the fast bed reactor. Thus, according to an embodiment of the invention, the outside heat-exchanger can be replaced by any other device capable of performing the primary function, as long as it does not significantly damage the purpose of the invention. Accordingly, the outside heat-exchanger may be replaced with an internal heat-exchanger.

The present invention does not set any special requirement on the light hydrocarbon feedstock, and the light hydrocarbon feedstock commonly used in the field can be used in the invention, and according to an embodiment of the invention, the light hydrocarbon feedstock is $C_4$-$C_6$ non-aromatic hydrocarbon mixture, and preferably, the light hydrocarbon feedstock at least comprises $C_4$-$C_6$ non-aromatic hydrocarbon mixture obtained from the separation unit.

According to an embodiment of the present invention, for the light hydrocarbon feedstock, a $C_4$-$C_6$ non-aromatic hydrocarbon mixture coming from the separation unit accounts for greater than 20 wt %, and the remaining of the $C_4$-$C_6$ non-aromatic hydrocarbon mixture comes from a catalytic cracking and/or steam cracking unit.

In the present invention, the composition of the $C_4$-$C_6$ non-aromatic hydrocarbon mixture may, for example, contain one or more of isobutene, 1-butene, n-butane, isobutane, isopentene, n-pentene, n-pentane, n-hexene, and isohexene.

In the present invention, the composition of the oxygenate feedstock is not particularly limited, and any mixture commonly used in the art comprising water and an oxygenate may be used in the present invention, and for the present invention, it is preferable that the oxygenate feedstock comprises oxygenate in an amount of 5 to 60 wt %, and water in an amount of 40 to 95 wt %.

In the present invention, the category of the oxygenate is widely selected, and according to an embodiment of the present invention, the oxygenate contains methanol and one or more of ethanol, propanol, butanol, acetaldehyde, propionaldehyde, butyraldehyde, acetone, butanone, formic acid, acetic acid, and propionic acid; preferably, the oxygenate comprise the aldehyde and/or ketone in an amount of 30 to 90 wt %.

According to one variation of the embodiment of the invention, the riser 203 is provided with an oxygenate or light hydrocarbon feed inlet, for reacting with the regenerated catalyst to obtain an additional reaction product comprising ethylene-propylene.

The type of the heat-removing medium 19 is not limited by the present invention, and any medium capable of providing heat, such as water, may be used. For illustration, the heat-removing medium used in Examples is water.

In the present invention, the operation conditions within the fast bed reactor 201 is not specially limited, and any operation conditions generally used in the art can be adopted. According to an embodiment of the present invention, the fast bed reactor 201 is operated at a catalyst temperature of 450 to 500° C., a gas linear velocity of 0.8 to 3 m/s, a reaction gauge pressure of 0.01 to 0.5 MPa, and a catalyst density of 50 to 250 kg/m³.

According to the invention, the purpose of the invention can be achieved by additionally arranging an outside riser reactor and operating according to the process of the invention, without special requirement on the operation conditions in the outside riser reactor 205, and for the invention preferably, in the outside riser reactor 205, the temperature of the catalyst is 530-650° C., the gas linear velocity is 1.1-15 m/s, and the catalyst density is 20-100 kg/m³.

According to a preferred embodiment of the invention, in step b): the weight ratio between the first part (stream 9-1) of the mixed catalyst in the fast bed settler 202 fed into the stripper, the second part (stream 9-2) of the mixed catalyst returned to the reaction section of the fast bed reactor 201, and the third part (stream 9-3) of the mixed catalyst fed into the outside heat-exchanger is (0.5-1):(5-7):(2-4.5).

According to a preferred embodiment of the invention, in step d): the weight ratio of the first part (stream 10-1) of the second particulate catalyst fed into the stripper to the second part (stream 10-2) of the second particulate catalyst fed into the riser 203 is (1-3):(7-9).

According to an embodiment of the invention, the weight ratio of the light hydrocarbon feedstock to the oxygenate feedstock is 1:(0.5-3). The ethylene-propylene yield can be improved by the preferred embodiment described above.

According to the present invention, preferably, the catalyst is a molecular sieve catalyst.

According to the present invention, preferably, the molecular sieve catalyst is at least one of a SAPO-34 molecular sieve catalyst, a ZSM-5 molecular sieve catalyst and a β molecular sieve catalyst, more preferably a SAPO-34 molecular sieve catalyst. Using the preferred embodiment of the invention, the conversion and the yield of the lower olefin are improved.

According to an embodiment of the invention, the regenerated catalyst has a carbon content of less than 0.1% by weight, based on the total weight of the catalyst.

According to an embodiment of the invention, the riser lifting medium is not specially limited and may be, for example, steam and/or the oxygenate feedstock and/or the light hydrocarbon feedstock.

The invention mainly modifies the structure and the operation procedures of the reaction system, and the rest operation conditions, processes and steps which are not particularly described can adopt the conventional processes, conditions and steps.

In the invention, the total yield of the ethylene and propylene, calculated as carbon, calculated as carbon, is calculated by: (the total yield of the ethylene and propylene calculated as carbon, calculated as carbon,)=(the weight of the ethylene and the propylene)/(the weight of the methanol feed calculated as carbon, calculated as carbon,)×100%.

(the weight of the methanol feed calculated as carbon, calculated as carbon,)=(the weight of the methanol feed) *14/32.

Thus, the present invention provides a number of embodiments of a first exemplary series, including:

1. A process for producing ethylene-propylene, comprising:

a) feeding a methanol feedstock (14) into the bottom of a fast bed reactor (201) to be contacted and reacted with a catalyst to obtain a reaction product I and a first particulate catalyst obtained from partial inactivation of the catalyst, both being delivered upward into a fast bed settler (202);

b) feeding an oxygenate feedstock (15) and/or a light hydrocarbon feedstock (16) into the bottom of an outside riser reactor (205) to be contacted and reacted with a regenerated catalyst to obtain a reaction product II and a second particulate catalyst (10), both being delivered upward into a riser settler (206);

c) feeding a second part (10-2) of the second particulate catalyst into the bottom of the riser (203), which is optionally contacted and reacted with the oxygenate feedstock (15) and/or a light hydrocarbon feedstock (16), to produce a mixture of a reaction product III and a third particulate catalyst, wherein the second part of the second particulate catalyst or optionally the mixture of the reaction product III and the third particulate catalyst are delivered upward into the fast bed settler (202);

d) mixing the first particulate catalyst with the second particulate catalyst or optionally with the third particulate catalyst in the fast bed settler to obtain a mixed catalyst (9), and feeding a first part of the mixed catalyst and a first part of the second particulate catalyst into a regenerator respectively for regeneration to obtain the regenerated catalyst; and wherein the oxygenate feedstock contains water and oxygenates, wherein the oxygenates are present in an amount of from 5 to 60 wt %, and the light hydrocarbon feedstock comprises a C4-C6 non-aromatic hydrocarbon mixture;

wherein the fast bed reactor (201), the fast bed settler (202) and the riser (203) are coaxially arranged, and the riser (203) is located, in the radial direction, inside the fast bed reactor (201).

2. The process according to embodiment 1 of the second exemplary series, wherein both the oxygenate feedstock (15) and the light hydrocarbon feedstock (16) are fed into the outside riser reactor (205), and neither the oxygenate feedstock (15) nor the light hydrocarbon feedstock (16) is fed into the riser (203).

3. The process according to embodiment 1 of the second exemplary series, wherein the light hydrocarbon feedstock (16) is fed into the outside riser reactor (205) and the oxygenate feedstock (15) is fed into the riser (203).

4. The process according to embodiment 1 of the second exemplary series, wherein both the oxygenate feedstock (15) and the light hydrocarbon feedstock (16) are fed into the outside riser reactor (205), and both the oxygenate feedstock (15) and the light hydrocarbon feedstock (16) are fed into the riser (203).

5. The process according to embodiment 1 of the second exemplary series, wherein the oxygenate feedstock (15) is fed into the outside riser reactor (205) and the light hydrocarbon feedstock (16) is fed into the riser (203).

6. The process according to embodiment 1 of the second exemplary series, wherein the ratio by weight of the flow rates entering the fast bed settler (202), Rw, of the second particulate catalyst or optionally a mixture of the reaction product III and the third particulate catalyst to the first particulate catalyst is 0.01<Rw≤0.5, preferably 0.02≤Rw≤0.2.

7. The process according to any one of the preceding embodiments of the second exemplary series, wherein the second part (9-2) of the mixed catalyst (9) is returned to the fast bed reactor (201), and the third part (9-3) of the mixed catalyst (9) is fed into the outside heat-exchanger (204); wherein the weight ratio of the first part, the second part and the third part of the catalyst (9) is (0.5-1):(5-7):(2-4.5).

8. The process according to any one of the preceding embodiments of the second exemplary series, wherein the weight ratio of the first part (10-1) to the second part (10-2) of the second particulate catalyst (10) is (1-3):(7-9).

9. The process according to any one of the preceding embodiments of the second exemplary series, wherein the first part of the mixed catalyst (9-1) and the first part of second particulate catalyst (10-1) are respectively fed into a stripper (7) for stripping before being respectively fed into a regenerator (8) for regeneration; wherein the both are stripped and then fed into the regenerator (8) in mixed form.

10. The process according to embodiment 1 of the second exemplary series, wherein the reaction product I, the reaction product II and the reaction product III are combined and then fed into a separation unit, to obtain a product rich in ethylene and propylene, $C_4$-$C_6$ non-aromatic hydrocarbon mixture and an aqueous phase by the separation;

the light hydrocarbon feedstock (16) is a $C_4$-$C_6$ non-aromatic hydrocarbon mixture, and preferably, the light hydrocarbon feedstock at least comprises a $C_4$-$C_6$ non-aromatic hydrocarbon mixture obtained from the separation unit; more preferably, for the light hydrocarbon feedstock (16), a $C_4$-$C_6$ non-aromatic hydrocarbon mixture coming from the separation unit accounts for greater than 20 wt %, and the remaining of the $C_4$-$C_6$ non-aromatic hydrocarbon mixture comes from a catalytic cracking and/or steam cracking unit; preferably, the C4-C6 non-aromatic hydrocarbon mixture comprises one or more of isobutene, 1-butene, n-butane, isobutane, isopentene, n-pentene, n-pentane, n-hexene, and isohexene;

the oxygenate mixture feedstock (15) comprises oxygenate in an amount of 5-60 wt % and water in an amount of 40-95 wt %; wherein the oxygenate contains methanol and one or more of ethanol, propanol, butanol, acetaldehyde, propionaldehyde, butyraldehyde, acetone, butanone, formic acid, acetic acid, and propionic acid; preferably, the oxygenate comprise the aldehyde and/or ketone in an amount of 30-90 wt %.

11. The process according to embodiment 1 of the second exemplary series, wherein, The fast bed reactor (201) is operated at a catalyst temperature of 450 to 500° C., a gas linear velocity of 0.8 to 3 m/s, a reaction gauge pressure of 0.01 to 0.5 MPa, and a catalyst density of 50 to 250 kg/m³; and/or The outside riser reactor (205) is operated at a temperature of the catalyst of 580-650° C., a gas linear velocity of 1.1-3 m/s, and a catalyst density of 50-100 kg/m³; and/or The riser (203) is operated at a temperature of the catalyst of 530-580° C., a gas linear velocity of 3-5 m/s, and a catalyst density of 20-80 kg/m³.

12. The process according to embodiment 1 of the second exemplary series, wherein, The catalyst is SAPO-34 molecular sieve catalyst; and/or The regenerated catalyst (27) has a carbon content of less than 0.1% by weight, based on the total weight of the catalyst.

13. A reaction system useful for the process for producing ethylene-propylene according to any one of the preceding embodiments of the second exemplary series, comprising: a fast bed reactor (201), a fast bed settler (202) and a riser (203) which are coaxially arranged; wherein The riser (203) is located, in the radial direction, within the fast bed reactor (201); the bottom of the riser (203) is provided with a riser feed inlet (210) for a lifting medium; the top outlet of the riser (203) is connected with a riser outlet structural member (208) through which the regenerated first particulate catalyst obtained by a regeneration treatment and optional other treatment is delivered into the fast bed settler (202);

the fast bed reactor (201) is used for allowing that contact and reaction of the feedstocks with the catalyst to produce ethylene-propylene is mainly carried out therein, during which reaction the catalyst is at least partially deactivated; the top of the fast bed reactor (201) is connected with a fast bed outlet structural member (207), through which a second particulate catalyst obtained from the partial deactivation is delivered into the fast bed settler (202) and is mixed with the regenerated first particulate catalyst to obtain a mixed catalyst;

the riser outlet structural member (208) and the fast bed outlet structural member (207) are both located within the fast bed settler (202), and the riser outlet structural member (208) is located above the fast bed outlet structural member (207);

wherein the riser outlet structural member (208) and the fast bed outlet structural member (207) are each preferably a fast separator.

14. The reaction system according to embodiment 13 of the second exemplary series, wherein the riser outlet structural member (208) and the fast bed outlet structural member (207) are each a fast separator; and The riser fast separator (208) consists of riser fast separator lower branch pipes (39) and riser fast separator horizontal pipes (40), wherein the riser fast separator horizontal pipes (40) are horizontally arranged, and the included angle between the riser fast separator lower branch pipe (39) and the riser fast separator horizontal pipe (40) is 90 degrees;

the fast bed fast separator (207) consists of fast bed fast separator lower branch pipes (38) and fast bed fast separator horizontal pipes (41), wherein the fast bed fast separator horizontal pipes (41) are horizontally arranged, and the included angle between the fast bed fast separator lower branch pipe (38) and the fast bed fast separator horizontal pipe (41) is 90 degrees.

15. The reaction system according to embodiment 14 of the second exemplary series, wherein the number, n, of the riser fast separator horizontal pipes (40) of the riser fast separator (208) is 2 to 8; and the included angle, β, between adjacent riser fast separator horizontal pipes (40) equals to 45-180 degrees; and/or The number, m, of the fast bed fast separator horizontal pipes (41) of the fast bed fast separator (207) is 2 to 8; and the included angle, α, between adjacent fast bed fast separator horizontal pipes (41) equals to 45-180 degrees.

16. The reaction system according to embodiment 14 of the second exemplary series, wherein the riser fast separator horizontal pipe (40) and the fast bed fast separator horizontal pipe (41) are distributed crosswise; and/or The ratio of the total cross-sectional area of the fast bed fast separator horizontal pipe (41) to the cross-sectional area of the fast bed reactor necking (42) is 1:1-3; and the ratio of the total cross-sectional area of the riser fast separator horizontal pipe (40) to the cross-sectional area of the riser (3) is 1:1-2.5.

17. The process according to embodiment 14 of the second exemplary series, wherein the ratio of the length of the fast bed fast separator horizontal pipe (41) to the length of the riser fast separator horizontal pipe (40) is (0.3-1):1;

the ratio of the length of the riser fast separator horizontal pipe (40) to the diameter of the second dense bed (2) is (0.8-0.2):1.

In addition, the present invention provides a number of embodiments of a second exemplary series, including:

1. A reaction system for producing ethylene-propylene, comprising: a fast bed reactor, a fast bed settler, a riser, an outside heat-exchanger, an outside riser reactor, a riser settler, a stripper and a regenerator; wherein:

The riser pipe is coaxial with the fast bed reactor and the fast bed settler, and the riser pipe is located inside the fast bed reactor;

the riser outlet is connected with the riser fast separator or the riser outlet structural member, and the top of the fast bed reactor is connected with a fast bed fast separator;

the riser fast separator and the fast bed fast separator are both located within the second dense bed, and the riser fast separator is located above the fast bed fast separator;

the riser outlet structural member is located inside the fast bed fast separator;

the outside riser reactor and the riser settler are coaxial, and the middle-upper part and the outlet of the outside riser reactor are located inside the riser settler;

wherein, the spent catalyst outlet of the riser settler is communicated with the feed inlet of the riser and is communicated with the feed inlet of the stripper, the spent catalyst outlet of the fast bed settler is communicated with the feed inlet of the stripper and is communicated with the feed inlet of the outside heat-exchanger, the solid outlet of the stripper is communicated with the solid feed inlet of the second dense bed, and the outlet of the heat-removed product of the outside heat-exchanger is communicated with the upper opening of the second dense bed.

2. The reaction system according to embodiment 1 of the second exemplary series, wherein, The riser fast separator consists of riser fast separator lower branch pipes and riser fast separator horizontal pipes, wherein the riser fast separator horizontal pipes are horizontally arranged, and the included angle between the riser fast separator lower branch pipe and the riser fast separator horizontal pipe is 90 degrees;

the riser fast separator lower branch pipes of the riser fast separator are uniformly distributed; and/or The number, n, of riser fast separator lower branch pipes of the riser fast separator is 2-8; and the included angle, β, between adjacent riser fast separator lower branch pipes equals to 45-180 degrees; and/or The fast bed fast separator consists of fast bed fast separator lower branch pipes and fast bed fast separator horizontal pipes, wherein the fast bed fast separator horizontal pipes are horizontally arranged, and the included angle between the fast bed fast separator lower branch pipe and the fast bed fast separator horizontal pipe is 90 degrees;

the fast bed fast separator lower branch pipes of the fast bed fast separator are uniformly distributed; and/or The number, m, of fast bed fast separator lower branch pipes of the fast bed fast separator is 2-8; and the included angle, α, between adjacent fast bed fast separator lower branch pipes equals to 45-180 degrees; and/or The riser fast separator lower branch pipes and the fast bed fast separator lower branch pipes are distributed crosswise.

3. The reaction system according to embodiment 1 or 2 of the second exemplary series, wherein the ratio between the distance from the center point of the fast bed fast separator to the center point of the fast bed fast separator lower branch pipe and the distance from the center point of the riser fast separator to the riser fast separator lower branch pipe is (0.3-1):1.

4. The reaction system according to any one of embodiments 1-3 of the second exemplary series, wherein the riser outlet structural member is composed of a diffusion cone and a diffusion plate, the riser outlet is connected to the diffusion cone, and the diffusion cone is connected to the diffusion plate; the distance between the riser outlet and the top of the fast bed fast separator lower branch pipe is h1, the distance from the connection point of the diffusion cone and the diffusion plate to the top of the fast bed fast separator lower branch pipe is h3, the distance between the edge point of the diffusion plate and the top of the fast bed fast separator lower branch pipe is h2, and the distance between the top of the fast bed fast separator and the top of the fast bed fast separator lower branch pipe is H; the included angle between the diffusion cone and the vertical direction is γ, and the included angle between the diffusion plate and the horizontal direction is δ; the ratio of h1 to H is (0.05-0.3):1, the ratio of h2 to H is (0.2-0.5):1, and the ratio of h3 to H is (0.4-0.6):1; h3 is greater than h2; γ is 10-60 degrees, and δ is 30-80 degrees.

5. A process for producing ethylene-propylene, the process being carried out in a reaction system according to any one of embodiments 1 to 4 of the second exemplary series, the process comprising:

a) feeding a methanol feedstock into a fast bed reactor to be contacted and reacted with a catalyst to obtain a reaction product I, and delivering upward the coked catalyst into a fast bed settler through a fast bed fast separator;

b) feeding a part of the mixed catalyst from the fast bed settler into a stripper, and returning a part of the mixed catalyst to the fast bed reactor, and feeding another part of the mixed catalyst into an outside heater to be contacted with a heat-removing medium for cooling followed be being returned to the fast bed reactor;

c) feeding a light hydrocarbon feedstock and a feedstock mixture into an outside riser reactor to contact with the catalyst, for reaction during the upward delivering thereof, and being fed into the riser settler, to obtain a reaction product II and a second particulate catalyst, wherein the feedstock mixture contains water and an oxygenate;

d) feeding a part of the second particulate catalyst from the riser settler into a stripper, and another part of the second particulate catalyst into the riser; wherein the second particulate catalyst fed into the riser enters the fast bed settler through the riser fast separator by the lifting of a riser lifting medium;

e) feeding the catalyst from the stripper, after being stripped by a stripping medium, into a regenerator to be contacted with a regeneration medium to burn coke on the catalyst to obtain a regenerated catalyst and flue gas;

f) degassing the regenerated catalyst and then feeding the degassed regenerated catalyst into the outside riser reactor; and feeding the reaction product I and the reaction product II together into a separation unit to obtain a product rich in ethylene and propylene, C4-C6 non-aromatic hydrocarbon mixture and an aqueous phase, wherein a part or all of the aqueous phase is used as the feedstock mixture.

6. The process according to embodiment 5 of the second exemplary series, wherein, the light hydrocarbon feedstock is a C4-C6 non-aromatic hydrocarbon mixture, and preferably, the light hydrocarbon feedstock at least comprises a C4-C6 non-aromatic hydrocarbon mixture obtained from the separation unit;

more preferably, for the light hydrocarbon feedstock, a C4-C6 non-aromatic hydrocarbon mixture coming from the separation unit accounts for greater than 20 wt %, and the remaining of the C4-C6 non-aromatic hydrocarbon mixture comes from a catalytic cracking and/or steam cracking unit;

preferably, the C4-C6 non-aromatic hydrocarbon mixture comprises one or more of isobutene, 1-butene, n-butane, isobutane, isopentene, n-pentene, n-pentane, n-hexene, and isohexene.

The feedstock mixture comprises oxygenate in an amount of 5-60 wt % and water in an amount of 40-95 wt %; wherein the oxygenate contains methanol and one or more of ethanol, propanol, butanol, acetaldehyde, propionaldehyde, butyraldehyde, acetone, butanone, formic acid, acetic acid, and propionic acid; preferably the oxygenate comprise the aldehyde and/or ketone in an amount of 30-90 wt %.

7. The process according to embodiment 5 or 6 of the second exemplary series, wherein, The fast bed reactor is operated at a catalyst temperature of 450 to 500° C., a gas linear velocity of 0.8 to 3 m/s, a reaction gauge pressure of 0.01 to 0.5 MPa, and a catalyst density of 50 to 250 kg/m$^3$; and/or The outside riser reactor is operated at a temperature of the catalyst of 530-650° C., a gas linear velocity of 1.1-15 m/s, and a catalyst density of 20-100 kg/m$^3$ and/or in step b): the weight ratio between the part of the mixed catalyst in the fast bed settler fed into the stripper, the part of the mixed catalyst in the fast bed settler returned to the fast bed reactor, and the part of the mixed catalyst in the fast bed settler fed into the outside heat-exchanger is (0.5-1):(5-7):(2-4.5);

in step d): the weight ratio of the part of the part of the second particulate catalyst fed into the stripper to the part of the second particulate catalyst fed into the riser 203 is (1-3):(7-9).

8. The process according to any one of the embodiments 5-7 of the second exemplary series, wherein the weight ratio of the light hydrocarbon feedstock to the feedstock mixture is 1:(0.5-3).

9. The process according to any one of embodiments 5-8 of the second exemplary series, wherein, The catalyst is SAPO-34 molecular sieve catalyst; and/or The regenerated catalyst has a carbon content of less than 0.1% by weight, based on the total weight of the catalyst.

10. The process according to any one of embodiments 5-9 of the second exemplary series, wherein the riser lifting medium is steam and/or feedstock mixture and/or light hydrocarbon feedstock.

EXAMPLE

The invention is further illustrated by, but is not limited to, the following Examples. In the Examples, reference is primarily made to the embodiment of the mixing device of the present invention for use in an ethylene-propylene reaction system as illustrated in FIG. 2; wherein the riser outlet structural member, fast bed outlet structural member, etc. are described with reference to the embodiments shown in FIG. 3-7.

Example 1

The device shown in FIG. 2 was used.

Referring to FIG. 4, the number, n, of the riser fast separator lower branch pipes 39 of the riser fast separator 208 was 2; and the included angle, β, between adjacent riser fast separator lower branch pipes 39 equaled to 180 degrees; the number, m, of the fast bed fast separator lower branch pipes 38 of the fast bed fast separator 207 was 2; and the included angle, α, between adjacent fast bed fast separator lower branch pipes 38 equaled to 180 degrees; and the riser fast separator lower branch pipe 39 and the fast bed fast separator lower branch pipe 38 were distributed crosswise.

The ratio between the distance from the center point of the fast bed fast separator 207 to the center point of the fast bed fast separator lower branch pipe 38 and the distance from the center point of the riser fast separator 208 to the riser fast separator lower branch pipe 39 was 0.8:1.

The process comprised:

a-1) feeding a methanol feedstock into the fast bed reactor 201 through the methanol feed inlet 209 to be contacted and reacted with a catalyst to obtain a reaction product I, from which a first particulate catalyst obtained from partial deactivation was delivered upward and was fed into a fast bed settler 202 through a fast bed fast separator 207;

a-2) feeding a first part of the mixed catalyst (stream 9-1) from the fast bed settler 202 into a stripper 7, and returning a second part (stream 9-2) of the mixed catalyst to the reaction section of the fast bed reactor 201, and feeding a third part (stream 9-3) of the mixed catalyst into an outside heat-exchanger 4 to be contacted with a heat-removing medium 19 for cooling followed be being returned to the fast bed reactor 201;

b-1) feeding a light hydrocarbon feedstock and an oxygenate feedstock into an outside riser reactor 205 to contact with the catalyst, for reaction during the upward delivering thereof, and being fed into the riser settler 206, to obtain a reaction product II and a second particulate catalyst, wherein the oxygenate feedstock contained water and an oxygenate;

c-1) for the second particulate catalyst from the riser settler 206, feeding a first part (stream 10-1) thereof into a stripper 7, and feeding a second part (stream 10-2) thereof into the riser 203; wherein the second particulate catalyst fed into the riser 203 enters the fast bed settler 202 through the riser fast separator 208 by the lifting of a riser lifting medium;

d-1) feeding the catalyst from the stripper, after being stripped by a stripping medium 24, into a regenerator to be contacted with a regeneration medium 26 to burn coke on the catalyst to obtain a regenerated catalyst 27 and flue gas 25; and d-2) degassing the regenerated catalyst 27 and then feeding the degassed regenerated catalyst into the outside riser reactor 205; and feeding through the product outlet 212 the reaction product I and the reaction product II together into a separation unit to obtain a product rich in ethylene and propylene, C$_4$-C$_6$ non-aromatic hydrocarbon mixture and an aqueous phase, wherein a part or all of the aqueous phase is used as the oxygenate feedstock.

In step b): the weight ratio between the first part (stream 9-1) of the mixed catalyst in the fast bed settler 202 fed into the stripper, the second part (stream 9-2) of the mixed catalyst returned to the fast bed reactor 201, and the third part (stream 9-3) of the mixed catalyst fed into the outside heat-exchanger was 0.8:6:3.2.

In step d): the weight ratio between the first part (stream 10-1) of the second particulate catalyst fed into the stripper and the second part (stream 10-2) of the second particulate catalyst fed into the riser 203 was 2:8.

The light hydrocarbon feedstock was C4-C6 non-aromatic hydrocarbon mixture obtained by the separation unit, comprising butylene in an amount of 60 wt %, pentene in an amount of 30 wt %, hexylene in an amount of 10 wt %; the oxygenate feedstock comprised oxides in a total amount of 50 wt %, wherein, the oxides comprised, by weight, methanol in an amount of 19%, ethanol in an amount of 5%, propanol in an amount of 3%, butanol in an amount of 2%, acetaldehyde in an amount of 8%, propionaldehyde in an amount of 2%, acetone in an amount of 40%, butanone in an amount of 20%, and formate in an amount of 1%.

The fast bed reactor 201 was operated at a catalyst temperature of 490° C., a gas linear velocity of 2 m/s, a reaction gauge pressure of 0.2 MPa, and a catalyst density of 70 kg/m$^3$; and the outside riser reactor 205 was operated at a temperature of the catalyst of 600° C., a gas linear velocity of 5 m/s, and a catalyst density of 40 kg/m$^3$.

The weight ratio of the light hydrocarbon feedstock to the oxygenate feedstock was 1:1.

The catalyst was SAPO-34 molecular sieve catalyst; and the regenerated catalyst 27 had a carbon content of 0.05% based on the total weight of the catalyst.

The riser lifting medium was steam.

In the Example, the total yield, calculated as carbon, of ethylene and propylene was 90.4 wt %.

Example 2

According to the process of Example 1, the device shown in FIG. 2 was used, except that the structure of the riser fast separator 208 shown in FIG. 4 was replaced with the structure of the riser outlet 208 shown in FIG. 6.

Among others, the ratio of h1 to H was 0.05:1, the ratio of h2 to H was 0.2:1, and the ratio of h3 to H was 0.4:1; γ was 60 degrees, and δ was 30 degrees.

The light hydrocarbon feedstock comprised butylene in an amount of 30 wt %, butane in an amount of 20 wt %, pentene in an amount of 45 wt %, hexylene in an amount of 5 wt %; and the oxygenate feedstock comprised oxides in a total amount of 60 wt %, wherein the oxides comprised, by weight, methanol in an amount of 5%, ethanol in an amount of 3%, propanol in an amount of 2%, acetaldehyde 20%, acetone in an amount of 50%, and butanone in an amount of 20%.

The fast bed reactor 201 was operated at a catalyst temperature of 490° C., a gas linear velocity of 2 m/s, a reaction gauge pressure of 0.2 MPa, and a catalyst density of 70 kg/m$^3$; and the outside riser reactor 205 was operated at a temperature of the catalyst of 600° C., a gas linear velocity of 5 m/s, and a catalyst density of 40 kg/m$^3$.

The weight ratio of the light hydrocarbon feedstock to the oxygenate feedstock was 1:1.

The catalyst was SAPO-34 molecular sieve catalyst; and the regenerated catalyst 27 had a carbon content of 0.05% based on the total weight of the catalyst.

The riser lifting medium was steam.

In the Example, the total yield, calculated as carbon, of ethylene and propylene was 89.3 wt %.

Example 3

Lower olefins were produced according to the system and process of Example 2, except that δ was 80°, γ was 10°, the ratio of h1 to H was 0.3:1, the ratio of h2 to H was 0.5:1, and the ratio of h3 to H was 0.6:1; while the rest was the same as in Example 2.

In the Example, the total yield, calculated as carbon, of ethylene and propylene was 90.1 wt %.

Example 4

Lower olefins were produced according to the system and process of Example 2, except that δ was 90 degree, γ was 70 degree, the ratio of h1 to H was 0.4:1, the ratio of h2 to H was 0.1:1, and the ratio of h3 to H was 0.3:1; while the rest was the same as in Example 2.

In the Example, the total yield, calculated as carbon, of ethylene and propylene was 86.3 wt %.

Example 5

Lower olefins were produced according to the system and process of Example 1, except that the number, n, of the riser fast separator lower branch pipes 39 of the riser fast separator 208 was 8; and the included angle, β, between adjacent riser fast separator lower branch pipes 39 equaled to 45 degrees; the number, m, of the fast bed fast separator lower branch pipes 38 of the fast bed fast separator 207 was 8; and the included angle, α, between adjacent fast bed fast separator lower branch pipes 38 equaled to 45 degrees; and the riser fast separator lower branch pipe 39 and the fast bed fast separator lower branch pipe 38 were distributed crosswise. The ratio between the distance from the center point of the fast bed fast separator 207 to the center point of the fast bed fast separator lower branch pipe 38 and the distance from the center point of the riser fast separator 208 to the riser fast separator lower branch pipe 39 was 1:1.

In the Example, the total yield, calculated as carbon, of ethylene and propylene was 90.2 wt %.

Example 6

Lower olefins were produced according to the system and process of Example 1, except that the number, n, of the riser fast separator lower branch pipes 39 of the riser fast separator 208 was 10; and the included angle, β, between adjacent riser fast separator lower branch pipes 39 equaled to 18 degrees; the number, m, of the fast bed fast separator lower branch pipes 38 of the fast bed fast separator 207 was 10; and the included angle, α, between adjacent fast bed fast separator lower branch pipes 38 equaled to 18 degrees; and the riser fast separator lower branch pipe 39 and the fast bed fast separator lower branch pipe 38 were distributed crosswise. The ratio between the distance from the center point of the fast bed fast separator 207 to the center point of the fast bed fast separator lower branch pipe 38 and the distance from the center point of the riser fast separator 208 to the riser fast separator lower branch pipe 39 was 1.5:1.

In the Example, the total yield, calculated as carbon, of ethylene and propylene was 88.7 wt %.

Example 7

Lower olefins were produced according to the system and process of Example 1, except that the fast bed reactor 201 was operated at a catalyst temperature of 450° C., a gas linear velocity of 0.8 m/s, a reaction gauge pressure of 0.01 MPa, and a catalyst density of 250 kg/m³; and the outside riser reactor 205 was operated at a temperature of the catalyst of 530° C., a gas linear velocity of 1.1 m/s, and a catalyst density of 100 kg/m³.

In the Example, the total yield, calculated as carbon, of ethylene and propylene was 87.6 wt %.

Example 8

Lower olefins were produced according to the system and process of Example 1, except that the fast bed reactor 201 was operated at a catalyst temperature of 500° C., a gas linear velocity of 3 m/s, a reaction gauge pressure of 0.5 MPa, and a catalyst density of 50 kg/m³; and the outside riser reactor 205 was operated at a temperature of the catalyst of 650° C., a gas linear velocity of 15 m/s, and a catalyst density of 20 kg/m³.

In the Example, the total yield, calculated as carbon, of ethylene and propylene was 89.1 wt %.

Example 9

Lower olefins were produced according to the system and process of Example 1, except that the number, n, of the riser fast separator lower branch pipes 39 of the riser fast separator 208 was 1; the number, m, of the fast bed fast separator lower branch pipes 38 of the fast bed fast separator 207 was 1; and the fast bed fast separator lower branch pipe 38 and the riser fast separator lower branch pipe 39 were aligned in line.

In the Example, the total yield, calculated as carbon, of ethylene and propylene was only 84.1 wt %.

Comparative Example 1

Example 1 was repeated, except that the outside riser reactor 205 and riser settler 206 were absent, and the regenerated catalyst 27 was fed directly into the fast bed reactor 201 to participate in the reaction.

In the Example, the total yield, calculated as carbon, of ethylene and propylene was only 82.4 wt %.

Comparative Example 2

Lower olefins were produced according to the system and process of Example 1, except that the riser 203 and the fast separator configuration were absent, while the second particulate catalyst (stream 10) was fed directly into the fast bed reactor 201.

In the Example, the total yield, calculated as carbon, of ethylene and propylene was 85.2 wt %.

Comparative Example 3

Example 2 was repeated, except that the outlet of the outside riser reactor 3 was connected directly with the fast bed settler 202.

In the Example, the total yield, calculated as carbon, of ethylene and propylene was only 83.3 wt %.

The preferred embodiments of the present invention have been described in detail above with reference to the accompanying drawings, but the present invention is not limited thereto. Within the scope of the technical idea of the invention, numerous simple variants are possible, comprising the combination of the individual specific technical features in any suitable manner. The various potential combination manners of the present invention are not described in detail in order to avoid unnecessary repetition. Such simple modifications and combinations should also be considered as disclosed in the present invention, and all such modifications and combinations are intended to be included within the scope of the present invention.

The invention claimed is:

1. A process for producing ethylene-propylene in a reaction system comprising a first reactor and a second reactor, the first reactor comprising a fast bed reactor, a fast bed settler, and a first riser tube, the second reactor comprising a second riser tube and a riser settler, comprising:

a) in the first reactor, feeding a methanol feedstock and a catalyst into the fast bed reactor, obtaining a reaction product I and a first particulate catalyst produced by partial inactivation of the catalyst, which exits from the fast bed reactor and enters the fast bed settler;

b) in the second reactor, feeding a first feedstock and a regenerated catalyst into the second riser tube, producing a first mixture comprising a reaction product II and a second particulate catalyst, wherein the first mixture exits the second riser tube and enters the riser settler to separate a reaction product II from the second particulate catalyst, separating the second particulate catalyst into a first part of the second particulate catalyst and a second part of the second particulate catalyst;

c) in the first reactor, feeding the second part of the second particulate catalyst into the first riser tube, producing a second mixture comprising a third particulate catalyst, wherein the second mixture exits the first riser tube and enters the fast bed settler; and d) obtaining a mixed catalyst comprising the first particulate catalyst the third particulate catalyst in the fast bed settler, and feeding a first part of the mixed catalyst and the first part of the second particulate catalyst into a regenerator for regeneration to obtain the regenerated catalyst, wherein the first feedstock is selected from an oxygenate feedstock, a light hydrocarbon feedstock, and a mixture thereof, the oxygenate feedstock comprises water and oxygenates, the oxygenates are present in an amount of from 5 to 60 wt % of the oxygenate feedstock, and the light hydrocarbon feedstock comprises a C4-C6 non-aromatic hydrocarbon mixture; and wherein the fast bed reactor, the fast bed settler and the first riser tube are coaxially arranged, and the first riser tube has a riser outlet, and the fast bed reactor has a fast bed outlet, and both the riser outlet and the fast bed outlet are disposed in the fast bed settler.

2. The process according to claim 1, wherein in step c), a second feedstock is fed into the first riser tube in the first reactor together with the second part of the second particulate catalyst, and the second mixture further comprises a reaction product III, wherein the second feedstock is the same or different from the first feedstock, and is independently selected from the oxygenate feedstock, the light hydrocarbon feedstock, and the mixture thereof.

3. The process according to claim 2, wherein the first feedstock to the second reactor is the light hydrocarbon feedstock, and the second feedstock to the first reactor is the oxygenate feedstock.

4. The process according to claim 2, wherein the first feedstock to the second reactor comprises the oxygenate feedstock and the light hydrocarbon feedstock, and the second feedstock to the first reactor comprises the oxygenate feedstock and the light hydrocarbon feedstock.

5. The process according to claim 2, wherein the first feedstock to the second reactor is the oxygenate feedstock, and the second feedstock to the first reactor is the light hydrocarbon feedstock.

6. The process according to claim 2, wherein Rw is a weight ratio of the second particulate catalyst or the mixture of the reaction product III and the third particulate catalyst to the first particulate catalyst, and has a value of 0.01<Rw≤0.5.

7. The process according to claim 1, wherein the first reactor further comprises an outside exchanger disposed in the fast settler and having an inlet connected to an outlet of the fast bed reactor, the process further comprising feeding a second part of the mixed catalyst to the fast bed reactor, and feeding a third part of the mixed catalyst into the outside heat-exchanger; and wherein a weight ratio of the first part, the second part, and the third part of the mixed catalyst is (0.5-1):(5-7):(2-4.5).

8. The process according to claim 1, wherein a weight ratio of the first part to the second part of the second particulate catalyst is (1-3):(7-9).

9. The process according to claim 1, further comprising feeding the first part of the mixed catalyst and the first part of second particulate catalyst into a stripper for stripping; and feeding the stripped catalyst from the stripper into the regenerator for regeneration.

10. The process according to claim 2, further comprising combining the reaction product I, the reaction product II and the reaction product III and then feeding the combination into a separation unit to obtain a product rich in ethylene and propylene, a C4-C6 non-aromatic hydrocarbon mixture, and an aqueous phase, wherein the oxygenates in the oxygenate feedstock contain methanol and one or more selected from ethanol, propanol, butanol, acetaldehyde, propionaldehyde, butyraldehyde, acetone, butanone, formic acid, acetic acid, and propionic acid.

11. The process according to claim 1, wherein, the fast bed reactor is operated at a catalyst temperature of 450 to 500° C., a gas linear velocity of 0.8 to 3 m/s, a reaction gauge pressure of 0.01 to 0.5 MPa, and a catalyst density of 50 to 250 kg/m$^3$; and/or the second reactor is operated at a temperature of the catalyst of 580-650° C., a gas linear velocity of 1.1-3 m/s, and a catalyst density of 50-100 kg/m$^3$; and/or the first riser tube is operated at a temperature of the catalyst of 530-580° C., a gas linear velocity of 3-5 m/s, and a catalyst density of 20-80 kg/m$^3$.

12. The process according to claim 1, wherein, the catalyst is SAPO-34 molecular sieve catalyst; and/or the regenerated catalyst has a carbon content of less than 0.1% by weight, based on the total weight of the catalyst.

13. The process according to claim 1, wherein the first feedstock to the second reactor comprises the oxygenate feedstock and the light hydrocarbon feedstock.

* * * * *